United States Patent [19]
Bressan

[11] Patent Number: 5,254,310
[45] Date of Patent: Oct. 19, 1993

[54] HIGH TEMPERATURE GENERALIZED CORROSION TEST INSTALLATION

[75] Inventor: Joelle A. Bressan, Rosny-sous-Bois, France

[73] Assignee: Gaz de France, Paris, France

[21] Appl. No.: 810,691

[22] Filed: Dec. 19, 1991

[30] Foreign Application Priority Data

Dec. 31, 1990 [FR] France ................. 90 16544

[51] Int. Cl.[5] ............... G01N 17/00; G01N 33/00
[52] U.S. Cl. .................... 422/53; 422/68.1;
422/82; 73/86; 436/6; 436/157; 374/57
[58] Field of Search ............ 422/53, 68.1, 82;
436/6, 157; 73/86, 865.6, 866.4; 374/57

[56] References Cited

U.S. PATENT DOCUMENTS

| Re. 32,625 | 3/1988 | Schwarz et al. | 374/57 |
| 3,685,969 | 8/1972 | Young, III | 422/53 |
| 3,922,903 | 12/1975 | Bornstein et al. | 422/53 |
| 3,957,440 | 5/1976 | Aussieker | 422/53 |
| 4,552,722 | 11/1985 | Fritscher et al. | 422/53 |
| 4,599,217 | 7/1986 | Winston et al. | 422/53 |
| 4,915,910 | 4/1990 | Manning et al. | 422/53 |

OTHER PUBLICATIONS

"Highly accelerated Temperature and humidity stress test technique", Gunn et al., IEEE/Proc., 1981, pp. 48–51.

Rice, D. W., et al., "Multiconcentration Low-Cost Environmental System" *IBM Technical Disclosure Bulletin*, vol. 17, No. 8, Jan. 1975, pp. 2426–2427.

Primary Examiner—James C. Housel
Assistant Examiner—Ramon Torres
Attorney, Agent, or Firm—Ladas & Parry

[57] ABSTRACT

The installation comprises a selective liquid-feeder assembly, a selective gas-feeder assembly for feeding gas under pressure, a mixing and preheating assembly itself comprising a vaporizing stage, a mixing stage, and a preheating stage to raise the gas-vapor mixture to a temperature of about 150° C. to about 300° C., and a distributor assembly for distributing the flow of gas-vapor mixture to a plurality of high temperature generalized corrosion test circuits. Each test circuit comprises a reactor including an intermediate preheater stage for preheating the gas-vapor mixture applied to the reactor to a temperature of about 400° C. to about 600° C., and a final heater stage containing at least one sample of material to be tested which sample is put into contact with the gas-vapor mixture flow from the intermediate preheater stage, and raised in the final heater stage to a temperature lying between about 700° C. and about 850° C.

14 Claims, 9 Drawing Sheets

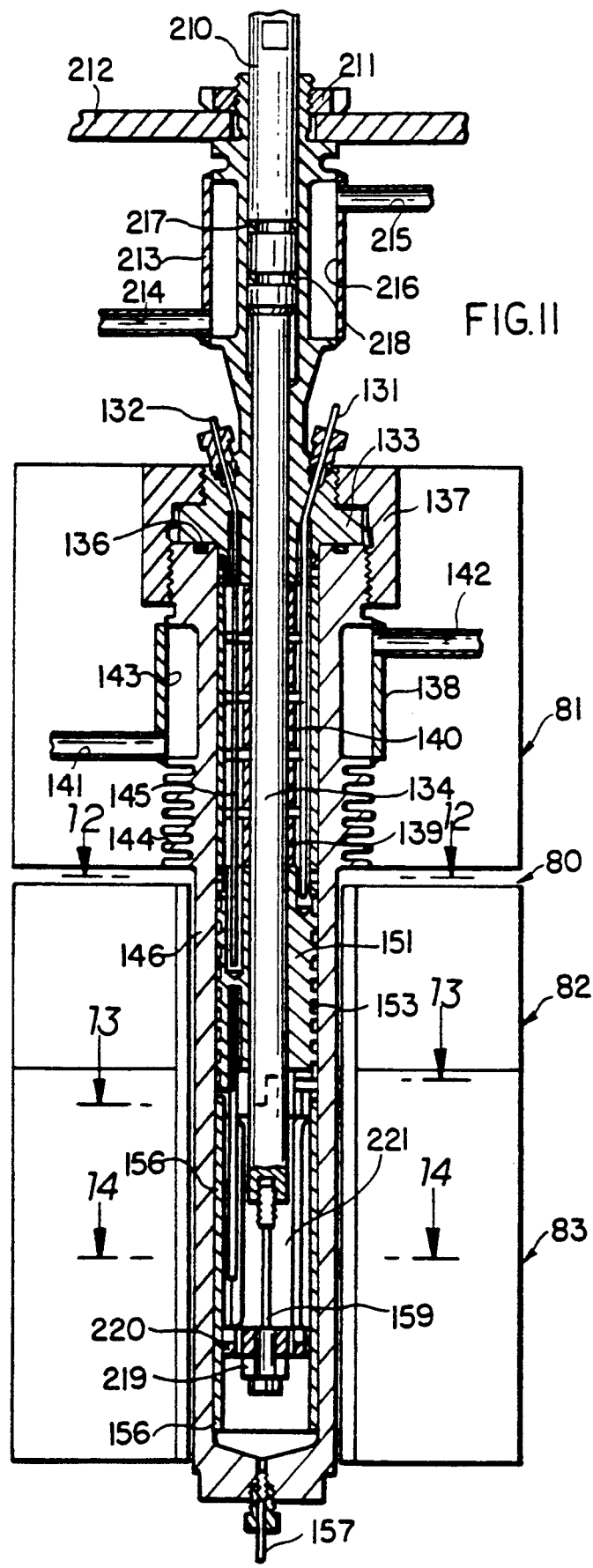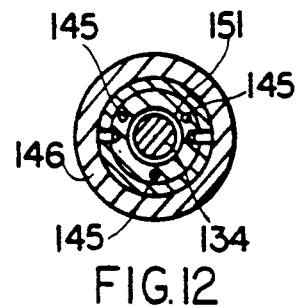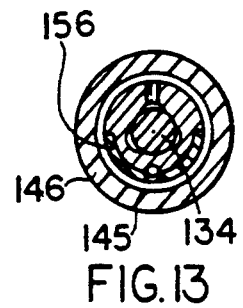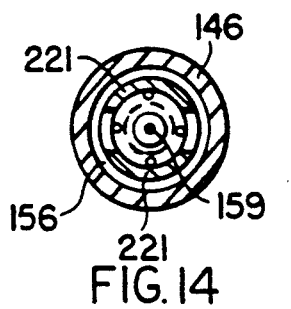

HIGH TEMPERATURE GENERALIZED CORROSION TEST INSTALLATION

The present invention relates to a test installation for the purpose of investigating high temperature generalized corrosion that may include corrosion under stress.

BACKGROUND OF THE INVENTION

Proposals have already been made to perform laboratory investigations of phenomena of localized corrosion by pitting, using glass-walled electrochemical cells under temperature conditions that do not exceed about 100° C.

Laboratory materials have also been made for investigating the phenomena of corrosion under stress under relatively severe environmental operating conditions corresponding to temperatures of less than 200° C. and pressures of less than 10 MPa. These materials comprise a single reactor whose structure is nevertheless not adapted to enable investigations to be performed of generalized corrosion at temperatures that may be in the order of about 600° C. to about 900° C.

That is why it has not been possible, heretofore, to investigate generalized corrosion phenomena in simple and convenient manner in the laboratory for temperatures going beyond about 200° C.

A specific object of the present invention is to remedy the above drawbacks and to make it possible to perform investigations of generalized corrosion under varying conditions of attack from liquid and gaseous media under pressure and at very high temperature, while nevertheless using an installation that is compact.

Another object of the invention is to make it possible both to investigate generalized corrosion and to investigate corrosion under stress using installations that are similar in design.

SUMMARY OF THE INVENTION

These objects are achieved by a high temperature generalized corrosion test installation comprising a selective liquid-feeder assembly, a selective gas-feeder assembly for feeding gas under pressure, a mixer and preheater assembly itself comprising a vaporizing stage for vaporizing the liquid received from the liquid-feeder assembly, a mixer stage for mixing the gases under pressure received from the gas-feeder assembly and the vapor produced in said vaporizing stage, and a preheater stage for preheating the gas-vapor mixture from said mixer stage to a temperature in the order 150° C. to 300° C., a distributor assembly for distributing the flow of gas-vapor mixture from the preheater stage to a plurality of high temperature generalized corrosion test circuits each comprising a reactor including an intermediate preheater stage for preheating the gas-vapor mixture applied to the reactor up to a temperature in the order of 400° C. to 600° C., and a final heater stage containing at least one sample of material to be tested which is put into contact with the flow of gas-vapor mixture from the intermediate preheater stage and raised in the final heater stage to a temperature lying between about 700° C. and about 850° C., cooling means for cooling the gas-vapor mixture from each of the test circuits, and a separator device for separately recovering the liquid phase and the gas phase from said gas-vapor mixture.

Advantageously, the distributor assembly comprises a removable distributor device disposed at the outlet from the preheater stage to produce a laminar flow or a turbulent flow.

The distributor assembly includes as many parallel pipes as there are test circuits, each provided with a respective electrical heater resistance, stop valve, and purge valve.

According to a particular feature, the installation includes liquid flow heat exchangers disposed between the distributor assembly and respective reactors to cool the removable portions of the test circuits that are external to the reactors to a temperature that is below about 200° C.

Each reactor comprises a single body in the form of the finger of a glove integrating the intermediate preheater stage and the final heater stage, and in which the various component parts are inserted from above.

Each reactor includes a ceramic lining level with the final heater stage.

To investigate generalized corrosion, the final heating stage of each reactor advantageously comprises a sample carrier on which the samples are disposed in a helical structure.

In an application to investigating corrosion under stress, the final heater stage of each reactor contains a single sample constituted by a traction test piece, and traction means are provided in each test circuit for applying a predetermined stress to each traction test piece.

Force and extension sensors are provided in each test circuit for monitoring traction and elongation exerted on each test piece in traction.

According to an advantageous feature, said traction means comprise traction servo motors and a voltage sawtooth generator for generating a continuous stress slope in controlled manner at a slow speed on the traction test piece under consideration.

The test installation may operate in an open loop or in a closed loop. With a closed loop, the gases delivered by the selective gas-feeder assembly for feeding gas under pressure are recycled to said assembly after passing through the test and cooling circuits.

According to a particular feature, said means for cooling the gas-vapor mixture from each test circuit comprise air cooled coils placed at the outlets of respective reactors together with a common water cooled circuit.

Preferably, the vaporizing stage is helical in structure for liquid flow with axial channels for gas flow.

By way of example, the test installation of the invention may comprise three to five test circuits.

In a particular embodiment, the preheater stage, the intermediate preheater stage, and the final heater stage are adapted to raise the gas-vapor mixture to the following temperatures respectively: about 200° C., about 500° C., and about 800° C.

BRIEF DESCRIPTION OF THE DRAWINGS

Embodiments of the invention are described by way of example with reference to the accompanying drawings, in which:

FIGS. 4, 5, and 6 are detailed views of a spacer mounted in the FIG. 3 assembly, FIGS. 4 and 6 being respectively a bottom view and a top view, while FIG. 5 is a section on line V—V of FIG. 4;

FIG. 11 is a more detailed axial section view of a reactor of the invention for investigating corrosion under stress and usable in the installation of FIG. 2;

FIGS. 12 to 14 are sections respectively on line XII—XII, XIII—XIII, and XIV—XIV of FIG. 11 for explaining the structure of the FIG. 11 reactor;

DETAILED DESCRIPTION

Figure 1:
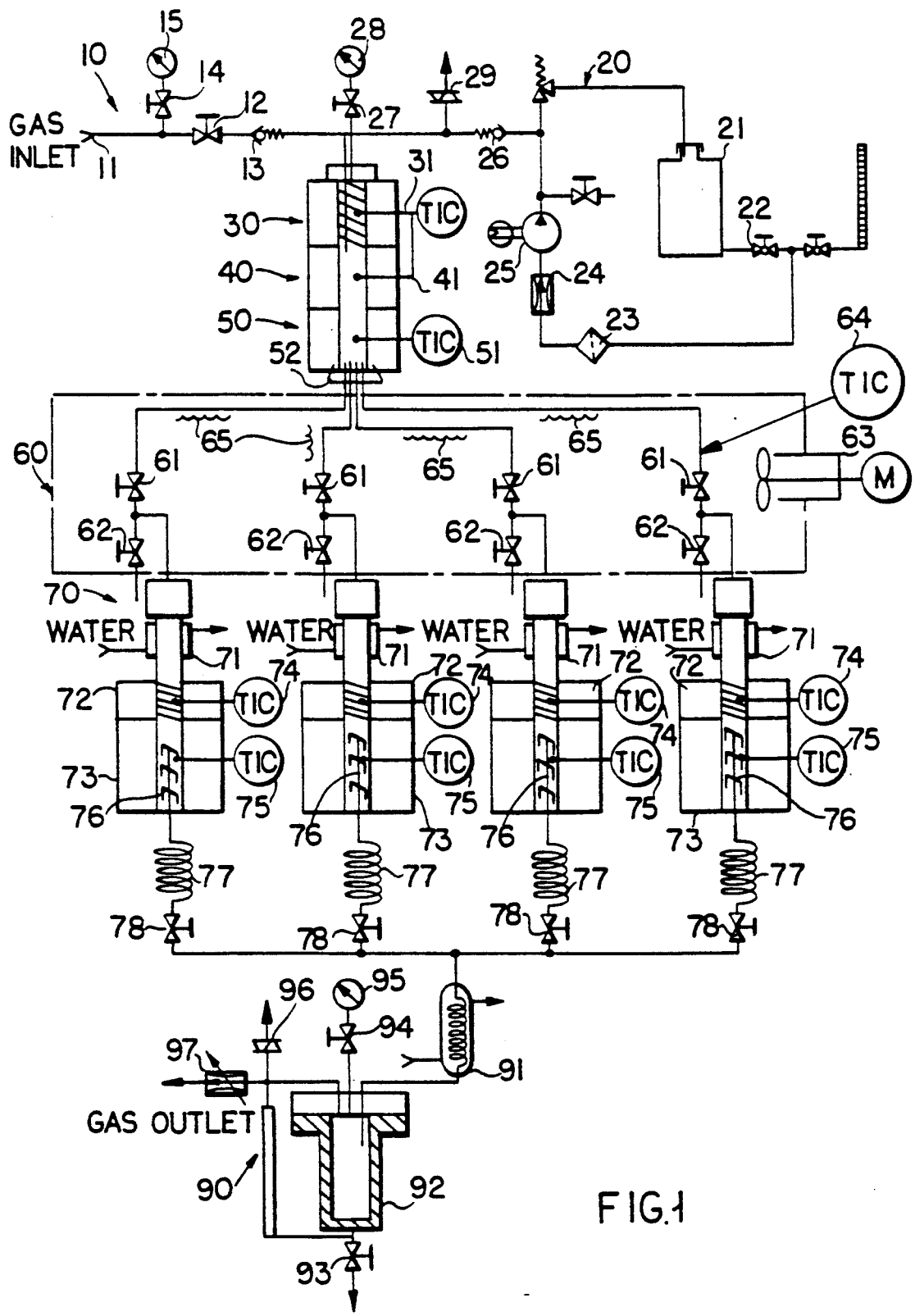
FIG. 1 is an overall diagram of a high temperature generalized corrosion test installation of the invention.

The installation of FIG. 1 comprises a selective liquid feeder assembly 20 having a tank 21 which may have a capacity of about 5 to 20 liters, for example, and which contains a supply of a liquid such as water. Liquid is selectively applied to the installation from the tank 21 via a circuit comprising a stop valve 22, a filter 23, a flow regulator 24, a pump 25, and a non-return valve 26. A pressure gauge 28 is connected by a valve 27 to the duct for feeding fluid to a vaporizing stage 30. The selective liquid-feeder assembly 20 also includes a drain 29, a purge valve, and a valve for providing connection with a level-detector member.

A gas-feeder assembly 10 for feeding gas under pressure, e.g. at pressures in the order of a few MPa, comprises a gas inlet pipe 11 for delivering gas from an outside source, a stop valve 12, a non-return valve 13, and a duct which passes down through the vaporizing stage 30 to open out into a stage 40 for mixing together the injected gases and the vapor produced from the injected liquid by the vaporizing stage 30.

A pressure gauge 15 connected to the gas inlet pipe 11 via a valve 14 serves to monitor the pressure which may be 3 MPa in an application to generalized corrosion at a temperature of about 800° C.

The gas-vapor mixture from the mixing stage 40 is applied to a preheater stage 50 for preheating the gas-vapor mixture from the mixing stage 40 to a temperature of about 150° C. to 300° C., e.g. to 200° C.

Thermocouples 31, 41, and 51 serve to monitor the temperature in the various stages of the vaporizing and mixing assembly 30, 40, and 50.

The preheater 50 advantageously incorporates a part 52 for distributing the flow which may be laminar or turbulent.

The assembly 60 essentially comprises a set of pipes fitted with electrical heater resistances 65 serving to convey the preheated gas-vapor mixture, e.g. at 200° C., selectively to various individual test circuits 70 per se.

The assembly 60 includes a fan device 63 and means 64 for monitoring temperature. Each pipe leading to a test circuit 70 includes a stop valve 61 and a purge valve 62.

Each test circuit 70 per se comprises an external apparatus head belonging to a reactor 72, 73 and provided with a liquid flow cooling circuit 71 for maintaining it at a temperature that is no greater than the outlet temperature of the preheater 50, e.g. 200° C.

The reactor of a test circuit 70 comprises an intermediate preheater stage 72 for preheating the gas-vapor mixture applied to the reactor to a temperature in the order of 400° C. to 600° C., e.g. 500° C., and a final heater stage 73 in which a set of samples 76 of the material to be tested is installed. The final heater stage 73 is constituted by an oven capable of raising the temperature of the gas-vapor mixture that is put into contact with the samples 76 to a temperature in the order of 700° C., to 850° C., e.g. 800° C.

Thermocouples 74 and 75 serve to monitor the temperature in the zones 72 and 73 of the reactor.

At the outlet from each reactor 72, 73, the gas-vapor mixture, e.g. raised to 800° C., is cooled in air-cooled coils 77 and is then delivered by a valve 78 to a second cooling circuit 91 which is common to all of the test circuits 70 and which has a flow of water as its coolant. The cooled fluid mixture is applied to a separator stage 90 and is introduced into a separator 92. The liquid phase is removed from the bottom of the separator 92 via a manual drawing-off valve 93, while the gas phase is removed from the top of the separator 92 via a drain 96 and a gas flow rate regulator 97 constituting an outlet which, when investigating generalized corrosion under stress, is not looped back to the inlet 11.

A pressure gauge 95 connected by a valve 94 to the separator 92 serves to monitor the pressure of the mixture while it is being separated.

Some of the component parts of the diagram of FIG. 1 are described in greater detail below with reference to FIGS. 3 to 10.

Figure 2:
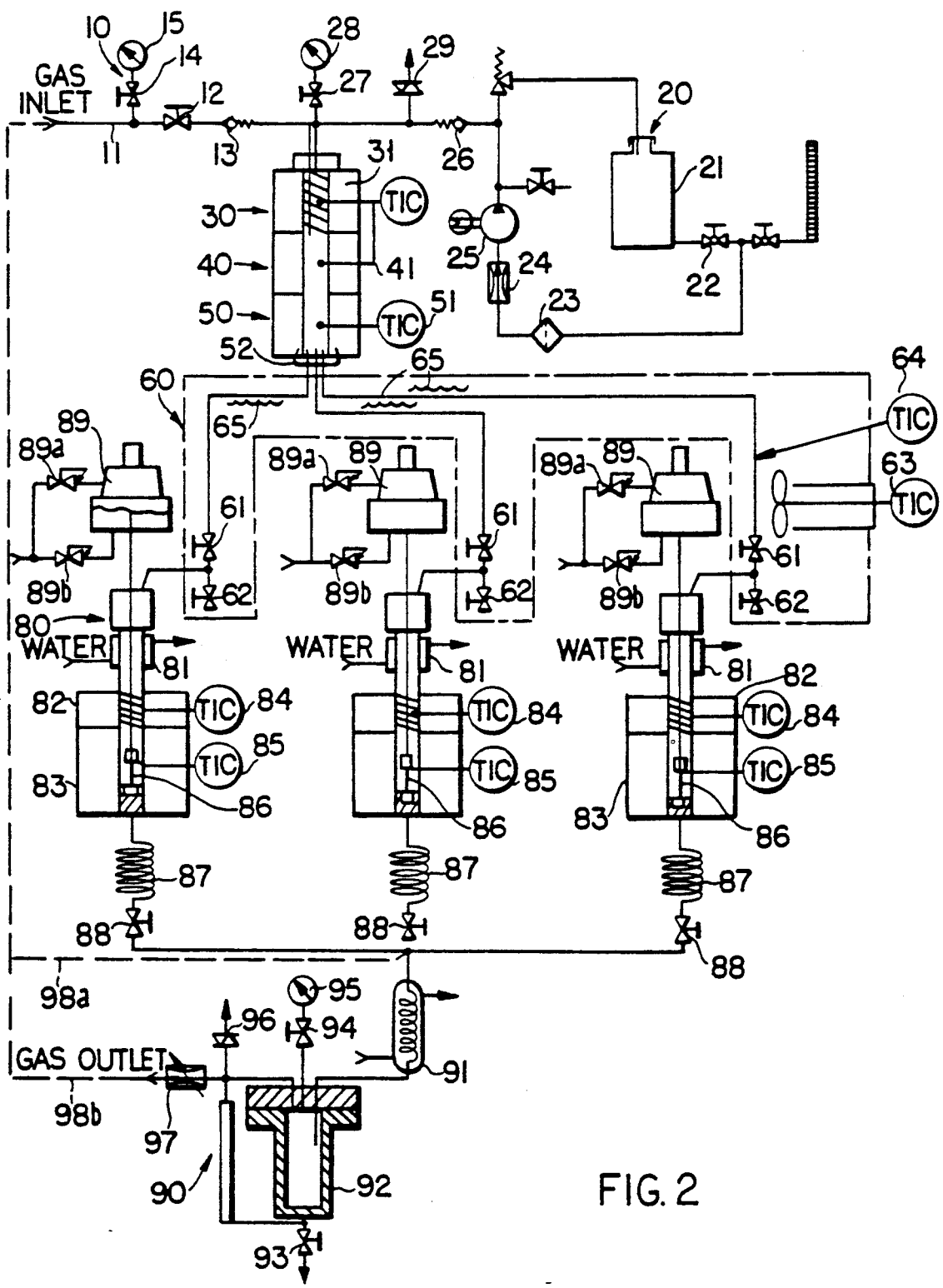
FIG. 2 is an overall diagram of a test installation of the invention applied more particularly to testing corrosion under stress.

FIG. 2 is an overall diagram of an installation for testing corrosion under stress and which has many points in common with the installation shown in FIG. 1, and as a result items that are common between them are given the same references and are not described again.

Thus, the selective gas-feeder assembly 10 for feeding gas under pressure, the selective liquid-feeder assembly 20, the assembly 30, 40, and 50 for vaporizing the mixture, and the assembly 60 for distributing the flow of mixture are entirely identical in the diagrams of both FIGS. 1 and 2, and for a circuit that uses the gases in an open loop, the same applies to the gas-liquid separator device 90.

The diagram of FIG. 2 differs in its test circuits 80 per se, which present various differences from the test circuits 70 of FIG. 1, while nevertheless still retaining numerous points in common.

Thus, the external head of each test circuit 80 includes a heat exchanger 81 through which a fluid flows and which is analogous to the heat exchanger 71 of FIG. 1.

Each reactor 82, 83 includes an intermediate heating stage 82 having a temperature-monitoring thermocouple 84 in a manner analogous to the reactors 72, 73 which have two stages 72 and 73 provided with thermocouples 74 and 75. The air-cooled coils 87 and the valves 88 also correspond to items 77 and 78 in FIG. 1.

The number of test circuits 70 and 80 in the example of FIG. 1 is four, whereas in the example of FIG. 2 there are three test circuits. Other numbers of test circuits may be used, e.g. two or five.

The installation of FIG. 2 differs from that of FIG. 1 essentially by the fact that each reactor 82, 83 contains a single sample 86 constituted by a traction test piece subjected to controlled traction forces exerted by a device 89 placed above the reactor and comprising, for example, traction servo motors 89a and 89b capable of acting upwards or downwards. This embodiment is described below in greater detail with reference to FIGS. 11 to 17.

In FIG. 2, it may be observed that the mixture of gases cooled in the coils 87 may be reinjected via the gas inlet 11 to constitute a closed loop as represented by dashed lined in the figure. Such reinjection may be performed from the outlet of the valve 88 (loop 98a) or from the outlet situated downstream from the regulator 97 (path 98b).

Figure 3:
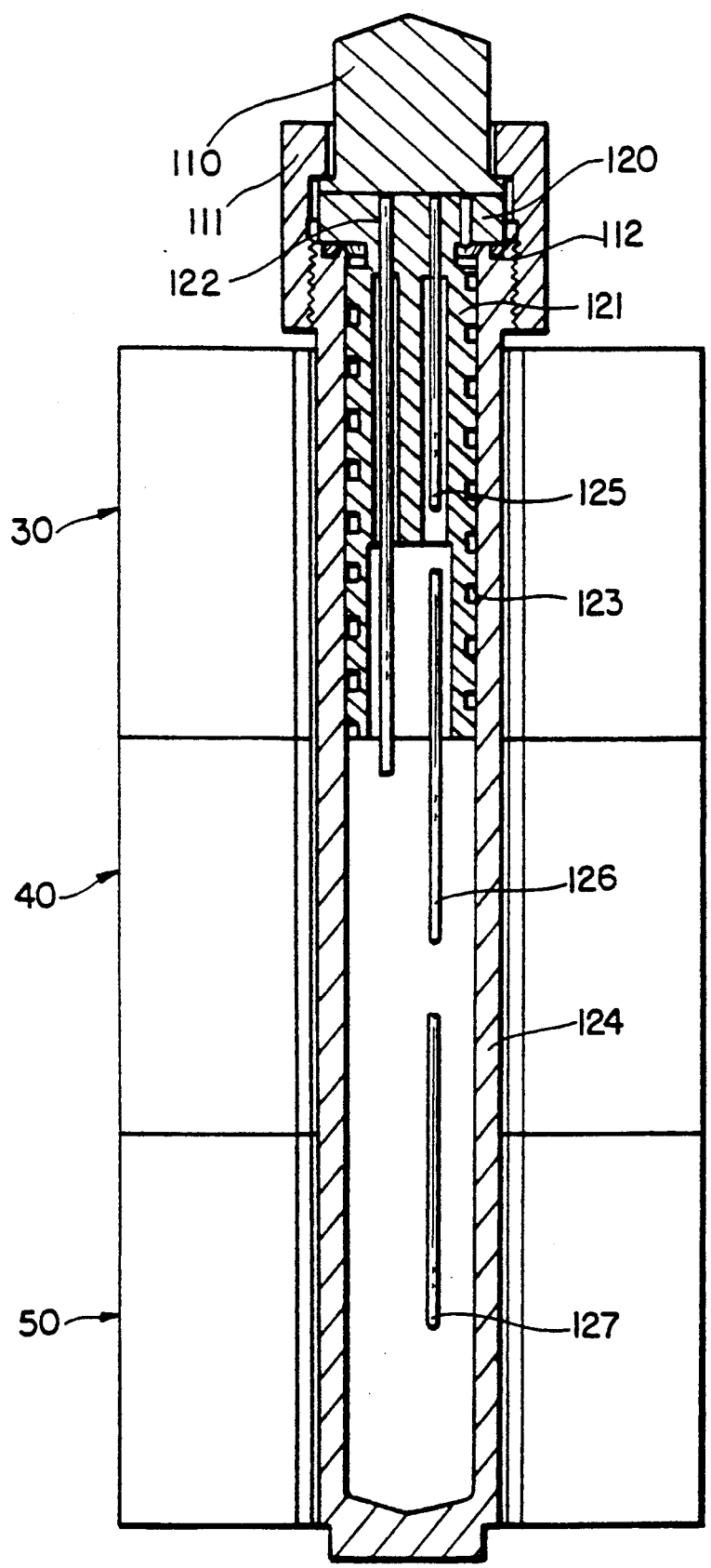
FIG. 3 is a view of a mixer and preheater assembly suitable for use in the installations of FIGS. 1 and 2.

FIG. 3 is an axial section through an example of the vaporizing and mixing device 30, 40, and 50. The vaporizing stage 30 presents a body 121 whose peripheral portion defines a helical screw pitch with passages 123 for the liquid to be vaporized. The body 121 has an axial channel 122 passing therethrough for transferring the gases under pressure that are chosen for establishing severe environmental conditions. These gases may be chemically aggressive gases such as chlorine or oxygen, for example. Additional axial passages are provided to receive thermocouples 125 to 127.

The vaporizer 30 is connected to the gas feeder assembly 10 and to the liquid-feeder assembly 20 via a spacer 110 which is held pressed against the head 120 of the plug constituting the body 121 of the vaporizer by means of a nut 111. An O-ring 112 is interposed between the head 120 of the body of the vaporizer 30 and the body 124 in the form of a finger of a glove which is common to all of the stages, i.e. the vaporizing stage 30, the mixing stage 40, and the preheating stage 50.

Figure 4:
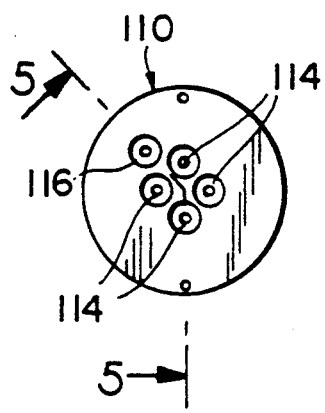
Figure 5:
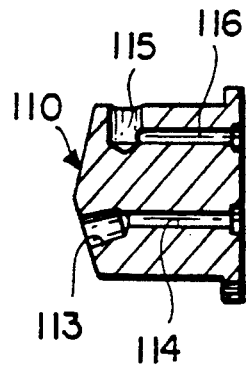
Figure 6:
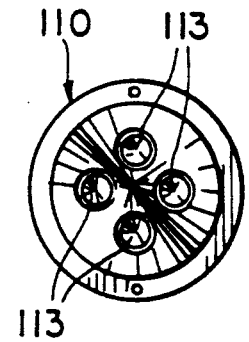

FIGS. 4 to 6 show further details of the channels 114 for applying gas through the spacer 110, and for passing the thermocouples 125 to 127, and the channel 116 for applying liquid into the spacer 110. It can be seen that the gas inlet pipe and the cables connected to the thermocouples may be connected to housings 113 formed in the sloping top faces of the spacer, while the liquid feeder pipe is connected laterally via a housing 115.

Figure 7:
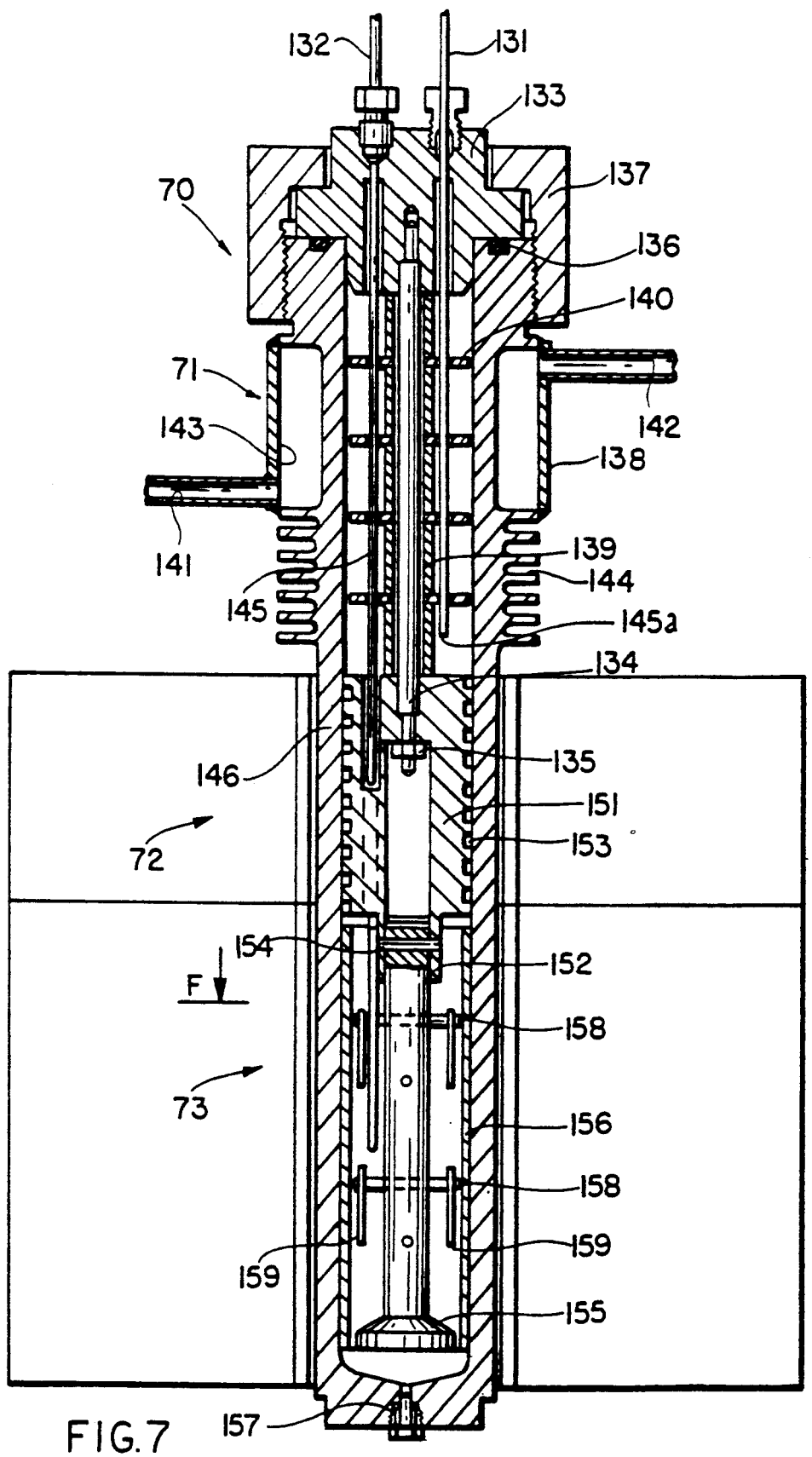
FIG. 7 is a more detailed axial section view through a generalized corrosion reactor of the invention usable in the FIG. 1 installation.

FIG. 7 shows one example of a generalized corrosion reactor. The reactor comprises a body 146 in the form of the finger of a glove and capable of being manually inserted without using special tooling in a housing formed in the intermediate preheating stage 72 and in the high temperature oven 73 per se.

Figure 9:
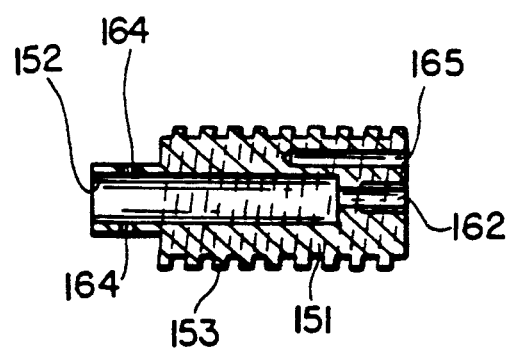
FIGS. 9 and 10 are respectively an elevation view and a bottom view of a heater device used in the FIG. 7 reactor at the intermediate preheater stage.
Figure 10:
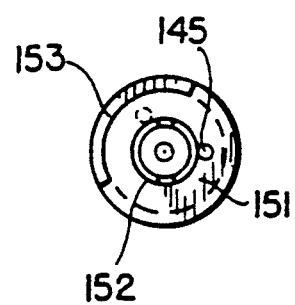
Figure 8:
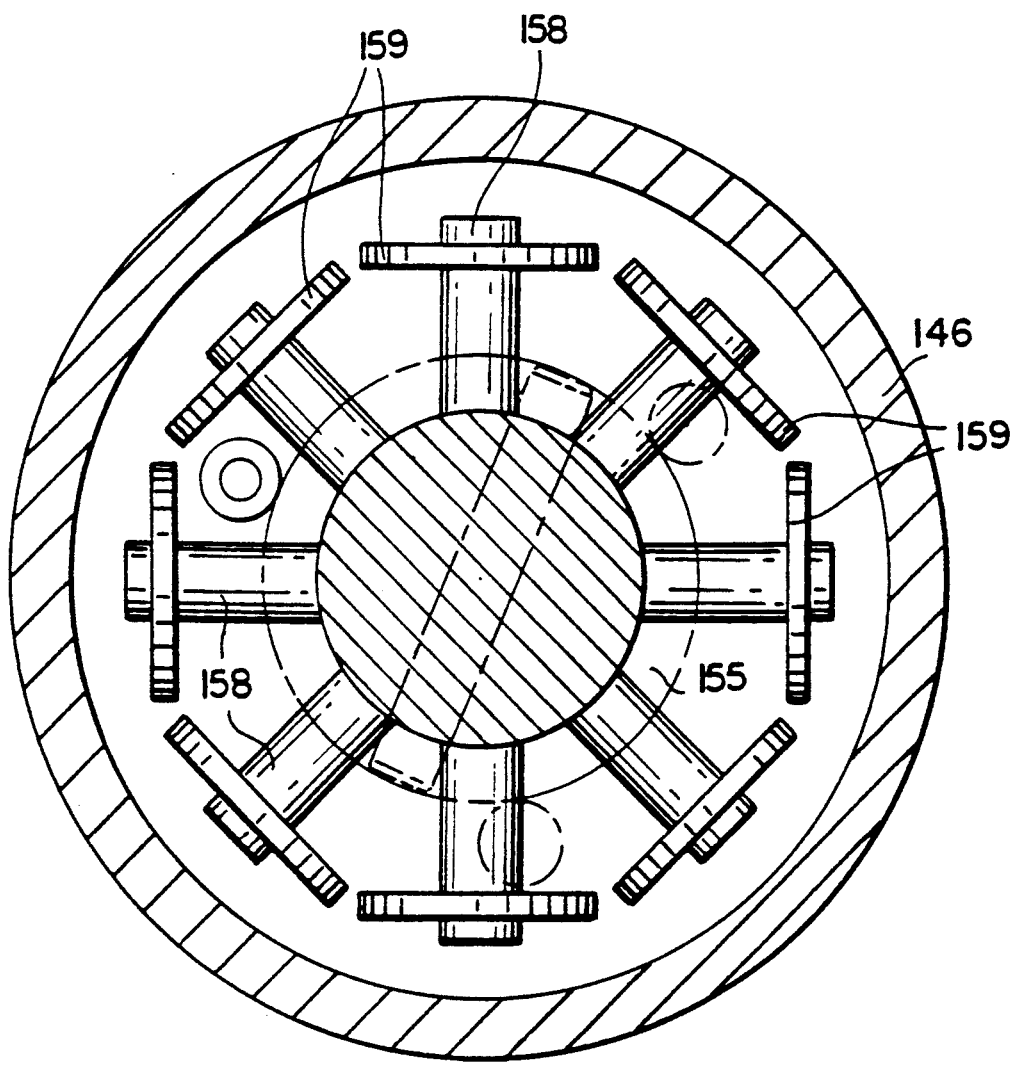
FIG. 8 is a section view of FIG. 7 on a larger scale and seen in the direction of arrow F, showing how the samples are positioned on a sample carrier.

The bottom portion of the body 146 is provided on the inside with a ceramic lining 156 which extends over the entire very high temperature portion thereof. The body 146 also has an orifice 157 formed through its end to exhaust the gas-vapor mixture after it has flowed over the samples 159 placed on a sample carrier 155. As shown in FIG. 8, the samples 159 are advantageously distributed helically around a support 155. The samples are held in place by pins 158. The sample carrier 155 is itself suspended by a shaft 154 engaged in holes 164 formed at the bottom portion 152 of the body 151 of a heater device in the intermediate preheating stage 72 which has an outside thread leaving helical passages 153 for the gaseous mixture. As shown in FIGS. 9 and 10, the heater device has axial channels 145 and 165 passing therethrough to receive thermocouples for measuring the temperature in the zones 72 and 73 of the reactor. An axial channel 162 formed in the top portion of the body 152 serves to pass the bottom end of a tie bar 134 provided with a nut 135 which fixes the heater 151 and the sample carrier 155 on a top plug 133 placed on the top face of the reactor body 146 with an interposed O-ring 136 and held in place by a nut 137. The plug 133 carries connection terminals for wires 131 and 132 that are connected to the temperature-measuring probes disposed in the zones 72 and 73 and also in the zone 145a situated immediately prior to the body 146 penetrating into the stage 72.

The portion of the reactor outside the intermediate preheater stage 72 comprises a cooling circuit 71 having a flow of liquid coolant and an outside jacket 138 leaving an annular space 143 around the body 146, together with a liquid feed pipe 141 and outlet pipe 142. Cooling fins 144 are advantageously formed on the body 146 beneath the heat exchanger 71.

A spacer 139 with the tie bar 134 passing therethrough is interposed between the body 151 of the heater and the plug 133. Washers 140 having orifices for passing the gaseous fluid are distributed between the heater body 151 and the plug 133.

FIGS. 11 to 14 show a test circuit 80 for investigating corrosion under stress.

In this case, the FIG. 7 tie bar 134 is replaced by a tie bar 134 which extends upwardly as far as an outlet shaft 210 of a traction mechanism, and downwardly to the top end of a single sample 159 which is in the form of a traction test piece, whose bottom portion is fixed by means of a key 219 and a washer 220 to the end of spacers 221 interposed between the bottom end of the test piece 159 and the bottom end of the heater body 152. The other component parts of the stages 81, 82, and 83 are similar to those described with reference to FIG. 7 and they are therefore given the same references.

The top end of the FIG. 11 tie bar 134 carries two O-rings 217 and 218, and it passes through an additional liquid flow heat exchanger having a jacket 213 that defines an annular chamber 216 and having inlet and outlet pipes 214 and 215. This additional heat exchanger is fixed by a nut 211 on a plate 212.

Figure 16:
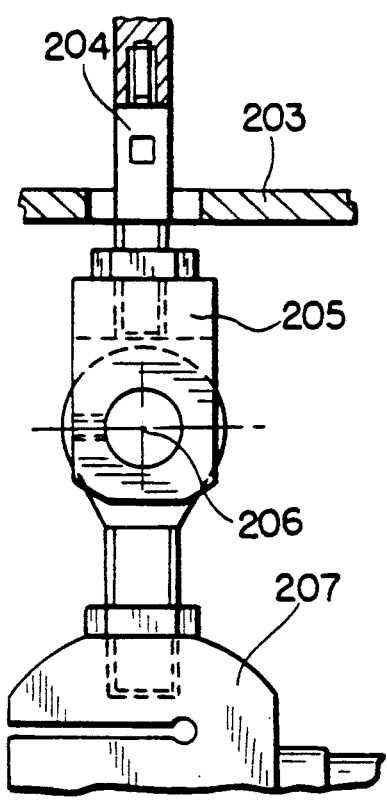
FIG. 16 is a detailed view showing a portion of the FIG. 15 device.
Figure 15:
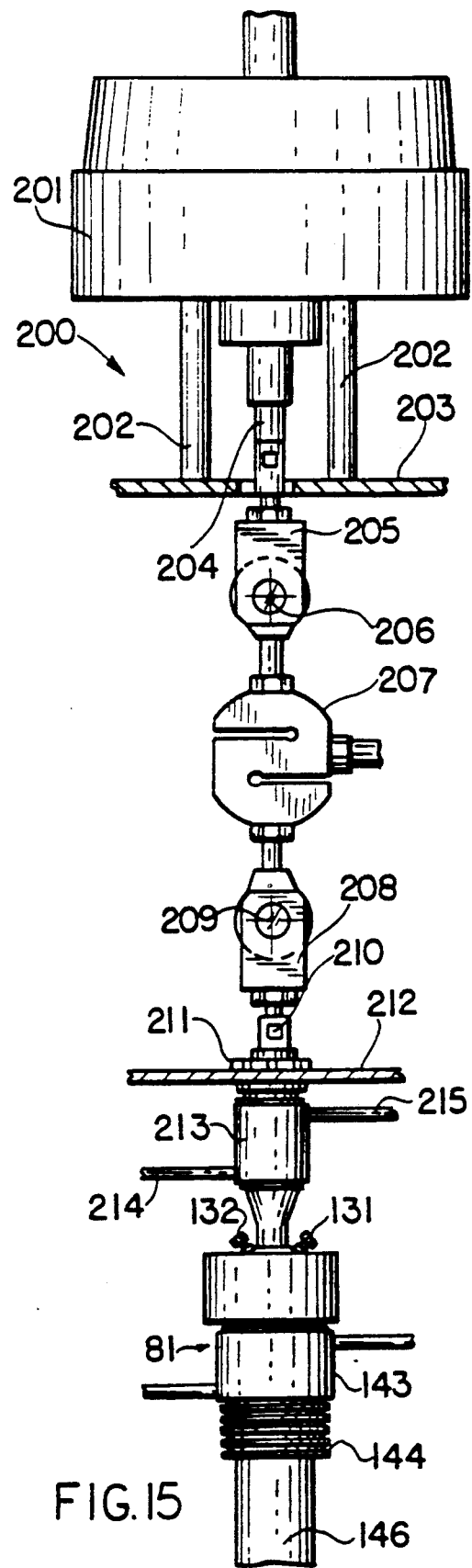
FIG. 15 is an elevation view showing an example of a traction device usable in the reactor for investigating corrosion under stress of FIG. 11.

FIGS. 15 and 16 show a traction device 200 comprising a set of servo motors 201 mounted by legs 202 on a frame 203 and exerting an adjustable traction force on a tie bar 204 which may also incorporate an extension sensor.

A force sensor 207 mounted between the tie bar 204 and the shaft 210 by hinges each including a fork 205 or 208 and a pin 206 or 209.

Figure 17:
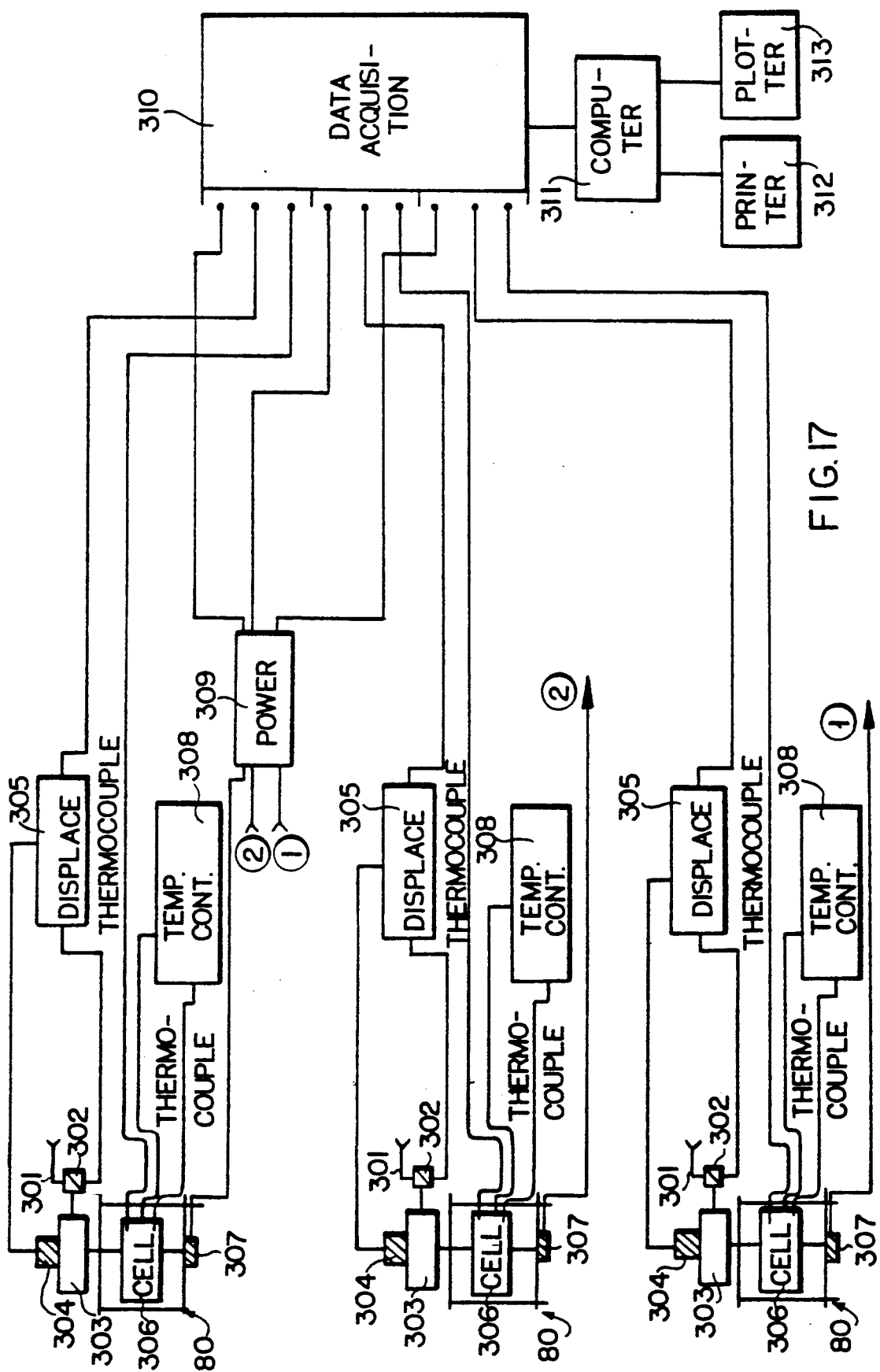
FIG. 17 is a diagram showing the servo-control circuits and the circuits for making use of the measurement signals in an installation for testing corrosion under stress such as the installation of FIG. 2.

FIG. 17 is an electrical circuit diagram of an embodiment of an installation for investigating corrosion under stress and having three test circuits, and thus three measurement cells.

FIG. 17 shows diagrammatically three measurement cells 306 each containing a test piece such as the test piece 86 of FIG. 2 for the sample 159 of FIG. 11 placed in a high temperature reactor 80. Reference 303 designates a traction mechanism with servo motors 302 fed with compressed air from a source 301. References 304 and 307 respectively designate a displacement sensor (i.e. an elongation sensor) and a force sensor. The force sensors 307 are powered from a power supply 309 whereas each displacement sensor 304 is powered by a displacement control device 305 which delivers a sawtooth voltage so as to exert a progressive stress on the measurement test piece 306, which stress increases at a predetermined slow speed.

The temperature measurement devices such as thermocouples and the oven heater means are connected to a temperature control circuit 308.

For each measurement cell, data relating to the temperature in the cell, to the force measured by the force sensor 307, and to the displacement measured by the displacement sensor 304 are delivered to a data acquisition circuit 310 which is itself connected to data processing and calculation circuits 311 connected to printer means 312 or to plotter means 313.

I claim:

1. A generalized corrosion test installation comprising:
    a selective liquid-feeder assembly for feeding a liquid;
    a selective gas-feeder assembly for feeding a gas under pressure; wherein, at least one of the liquid and the gas is corrosive;
    a mixer and preheater assembly comprising a vaporizing stage in fluid communication with the liquid-feeder assembly for vaporizing the fed liquid, a mixer stage in fluid communication with the gas-feeder assembly for mixing the gas and the vapor, and a preheater stage for preheating the gas-vapor mixture to a temperature on the order of from 150° C. to 300° C.;
    a distributor assembly for distributing a flow of the preheated gas-vapor mixture to a plurality of generalized corrosion test circuits each comprising a reactor including an intermediate preheater stage for intermediately preheating the gas-vapor mixture up to a temperature on the order of from 400° C. to 600° C. and a final heater stage for containing at least one sample of a material to be tested in contact with a final flow of the gas-vapor mixture and for raising the temperature of the final flow to a temperature between about 700° C. and about 850° C.;
    cooling means for cooling an outflow of the gas-vapor mixture from each of the test circuits; and
    a separator device for separately recovering the liquid phase and the gas phase from said gas-vapor mixture.

2. A test installation according to claim 1, wherein the distributor assembly comprises a removable flow distributor device disposed at an outlet from the preheater stage to make the flow one of laminar and turbulent.

3. A test installation according to claim 1, wherein the distributor assembly includes as many parallel pipes as there are test circuits, each provided with a respective electrical heater resistance, stop valve, and purge valve.

4. An installation according to claim 1, including liquid flow heat exchangers disposed between the distributor assembly and respective reactors to cool the removable portions of the test circuits that are external to the reactors to a temperature that is below about 200° C.

5. An installation according to claim 1, wherein each reactor comprises a single cylindrical container integrating at least the intermediate preheater stage and the final heater stage.

6. An installation according to claim 1, wherein each reactor includes a ceramic lining level with the final heater stage.

7. An installation according to claim 1, wherein the final heater stage of each reactor includes a sample carrier on which samples are disposed in a helical structure.

8. An installation according to claim 1, wherein the final heater stage of each reactor contains a single sample constituted by a traction test piece, and wherein traction means are provided in each test circuit for applying a predetermined stress to each traction test piece.

9. An installation according to claim 8, including force and extension sensors in each test circuit to monitor the traction and the elongation exerted on each traction test piece, wherein said traction means comprise traction servo motors and a voltage sawtooth generator for generating a continuous stress slope in controlled manner at a predetermined speed on the traction test piece under consideration.

10. An installation according to claim 8, including a closed loop for recycling the gases applied from said selective gas-feeder assembly for feeding gas under pressure.

11. An installation according to claim 1, wherein said means for cooling the gas-vapor mixture from each test circuit comprise air cooled coils placed at the outlets of respective reactors together with a common water cooled circuit.

12. An installation according to claim 1, wherein the vaporizing stage is helical in structure for liquid flow with axial channels for gas flow.

13. An installation according to claim 1, wherein it has between three and five test circuits.

14. An installation according to claim 1, wherein the preheater stage, the intermediate preheater stage, and the final heater stage are adapted to raise the gas-vapor mixture to the following temperatures respectively: about 200° C., about 500° C., and about 800° C.

* * * * *